US012273989B2

(12) United States Patent
Shinton et al.

(10) Patent No.: US 12,273,989 B2
(45) Date of Patent: Apr. 8, 2025

(54) LINAC JOINTS

(71) Applicant: Elekta Limited, Crawley (GB)

(72) Inventors: Ian Shinton, Crawley (GB); Shaikh Mohammad Ismail Abdul Gaffar, Crawley (GB)

(73) Assignee: Elekta Limited, Crawley (GB)

( * ) Notice: Subject to any disclaimer, the term of this patent is extended or adjusted under 35 U.S.C. 154(b) by 75 days.

(21) Appl. No.: 18/000,052

(22) PCT Filed: May 28, 2021

(86) PCT No.: PCT/EP2021/064455
§ 371 (c)(1),
(2) Date: Nov. 28, 2022

(87) PCT Pub. No.: WO2021/240002
PCT Pub. Date: Dec. 2, 2021

(65) Prior Publication Data
US 2023/0239991 A1    Jul. 27, 2023

(30) Foreign Application Priority Data
May 28, 2020   (GB) ..................................... 2007977

(51) Int. Cl.
*H05H 7/22*   (2006.01)
*A61N 5/10*   (2006.01)
(Continued)

(52) U.S. Cl.
CPC ............. *H05H 7/22* (2013.01); *A61N 5/1078* (2013.01); *H01P 1/042* (2013.01); *H01P 3/12* (2013.01);
(Continued)

(58) Field of Classification Search
CPC .. H05H 7/22; H05H 7/02; H05H 9/00; H05H 2007/025; H05H 2277/11; H05H 9/048;
(Continued)

(56) References Cited

U.S. PATENT DOCUMENTS

| 2,685,069 | A | | 7/1954 | Ingraham | |
| 2,933,442 | A | * | 4/1960 | Lawrence | ................. H05H 6/00 |
| | | | | | 376/193 |

(Continued)

FOREIGN PATENT DOCUMENTS

| CN | 104812444 | A | * | 7/2015 | ........... A61N 5/1077 |
| CN | 110710335 | A | * | 1/2020 | ........... A61N 5/1077 |

(Continued)

OTHER PUBLICATIONS

"International Application Serial No. PCT/EP2021/064455, International Search Report dated Oct. 5, 2021", (Oct. 5, 2021), 5 pgs.
(Continued)

*Primary Examiner* — Abdullah A Riyami
*Assistant Examiner* — Syed M Kaiser
(74) *Attorney, Agent, or Firm* — Schwegman Lundberg & Woessner, P.A.

(57) ABSTRACT

A reusable joint for a medical linac, a reusable CF choke flange for a medical linac, a linac and a method for forming a reusable joint for a medical linac are disclosed. The reusable joint comprises a CF choke flange, a CF cover flange and a gasket. The CF choke flange comprises a first waveguide aperture, a choke groove and a first CF groove comprising a first knife-edge, wherein the choke groove is disposed radially inwards from the first CF groove on the CF choke flange. The CF cover flange comprises a second waveguide aperture aligned with the first waveguide aperture and a second CF groove comprising a second knife-edge and aligned with the first CF groove. The gasket is (Continued)

disposed between and in contact with the first CF groove and the second CF groove.

20 Claims, 13 Drawing Sheets

(51) Int. Cl.
  *H01P 1/04* (2006.01)
  *H01P 3/12* (2006.01)
  *H05H 7/02* (2006.01)
  *H05H 9/00* (2006.01)

(52) U.S. Cl.
  CPC ............ *H05H 7/02* (2013.01); *H05H 9/00* (2013.01); *A61N 2005/1095* (2013.01); *H05H 2007/025* (2013.01); *H05H 2277/11* (2013.01)

(58) Field of Classification Search
  CPC .......... A61N 5/1078; A61N 2005/1095; A61N 5/1077; H01P 1/042; H01P 3/12; H01J 23/14
  See application file for complete search history.

(56) References Cited

U.S. PATENT DOCUMENTS

| | | | |
|---|---|---|---|
| 5,196,814 A | 3/1993 | Felker et al. | |
| 2004/0016892 A1* | 1/2004 | McIntyre | A61L 2/087 250/455.11 |
| 2021/0287825 A1* | 9/2021 | Figueroa Saavedra | A61N 5/1049 |

FOREIGN PATENT DOCUMENTS

| EP | 2819238 A1 | 12/2014 |
|---|---|---|
| KR | 20090132422 A | 12/2009 |
| WO | WO-2018175804 A1 | 9/2018 |

OTHER PUBLICATIONS

"International Application Serial No. PCT/EP2021/064455, Written Opinion dated Oct. 5, 2021", (Oct. 5, 2021), 9 pgs.

"United Kingdom Application Serial No. 2007977.8, Examination Report dated Nov. 26, 2020" (Nov. 26, 2020), 5 pgs.

Anonymous, "Vacuum flange—Wikipedia", Mar. 12, 2020, XP055843731 Retrieved from Internet: URL:https://en.wikipedia.org/w/index.php?title=vacuum_flange&oldid=95247433 [retrieved on Sep. 22, 2021], (Oct. 5, 2021), 5 pgs.

Ovchinnikova, L., et al., "Choke-type resonator for a compact storage ring", 29th Linear Accelerator Conf., (2019), 126-129.

Xiao, Binping P., et al., "Calorimeters for precision power dissipation measurements on controlled-temperature superconducting radiofrequency samples", Review of Scientific Instruments 83.12, (2012), pp. 124905.

Yeremian, A. D., et al., "Choke for standing wave structures and flanges", Proc. IPAC'10, Kyoto, Japan, (2010), 3 pgs.

* cited by examiner

LINAC JOINTS

PRIORITY APPLICATIONS

This application is a U.S. National Stage Filing under 35 U.S.C. § 371 from International Application No. PCT/EP2021/064455, filed on May 28, 2021, and published as WO2021/240002 on Dec. 2, 2021, which claims the benefit of priority to United Kingdom Application No. 2007977.8, filed on May 28, 2020; the benefit of priority of each of which is hereby claimed herein, and which applications and publication are hereby incorporated herein by reference in their entireties.

This disclosure relates to radiotherapy devices, and in particular to radiotherapy devices comprising linacs and linac joints.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

In high-power radiofrequency (RF) systems, arcing can occur due to imperfections in the inner surfaces of the RF waveguide. Arcing can be described as an electrical discharge or power breakdown, and can damage expensive RF power sources and other components of the RF system. In a typical linear accelerator, for example an ultra-high vacuum (UHV) linac, sections of the accelerating waveguide are brazed or welded together to present relatively smooth and continuous surfaces to radio frequency (RF) waves travelling in the interior of the waveguide. This can limit arcing. However, such brazed or welded connections are permanent connections, meaning that sections of the waveguide cannot be separated after brazing or welding without destroying or damaging the connection and/or the sections of the waveguide. Therefore, it is not possible to easily replace/repair damaged components such as targets, electron (particle) sources such as electron guns, and RF windows. Instead, a failure results in the entire linac being replaced or returned to the place of manufacture for reworking.

An RF choke is a reusable RF joint designed to suppress passage of high-frequency RF waves while allowing passage of lower frequency RF waves. An RF choke has a high inductance for such high-frequency RF waves. A traditional RF choke contains an O-ring seal. Such O-ring seals typically comprise a rubber O-ring in a groove on one or both of two faces that meet to form the joint. Use of the O-ring seal enables pressurisation of the waveguide. It is not possible to use such RF chokes in UHV regions since the O-ring seal leads to arcing when the voltage standing wave ratio (VSWR), which is a measure of the reflectance of a wave travelling through the waveguide, is swung too far (i.e. varied significantly). This arcing is due to both surface current and the small leak rate through the O-ring seal.

A CF joint (originally called a ConFlat joint, though the terms CF flange and CF joint are now well-known in the art) is a reusable joint that is UHV compatible. A CF joint has a sexless design in which both flanges forming the joint are identical. The CF joint comprises a gasket held in place between two knife-edges to provide a UHV seal. Such CF joints can be baked up to 500° C. However, such CF joints cannot be used in vacuum systems where there is a large potential frequency and VSWR change as in these conditions the joint may be damaged or destroyed due to a resonant RF frequency node and/or due to large surface currents forming at the joint. Instead, CF joints may be located on pumping flanges comprising round vacuum tubes that do not contain RF power. While there exist RF power variants of CF flanges, these can only be placed in a system where a null field is guaranteed due to the aforementioned reasons. While it may be intended that a location of a CF joint coincides with a location of null field under normal operation, such a CF joint may yet be damaged in the event of a high-power instability.

Some known designs use a choke mode cavity, i.e. a brazed cavity that relies on a choke mode to damp harmful higher order modes (HOMs) and lower order modes (LOMs) that can lead to beam breakup in large accelerating structures. These choke mode cavities are designed for the purpose of damping and typically contain a damping dielectric material to remove the unwanted trapped modes captured in the choke regions. These trapped modes are RF modes which reside within a region of the RF geometry without propagating therefrom, and which can be detrimental to the RF system by causing RF breakdown or beam breakup (BBU). A disadvantage of a typical choke mode cavity is that the Q factor (quality factor) and stored energy is much lower than in other accelerating cavity variants leading to a need for a longer accelerating structure to achieve a given acceleration of a charged particle.

It would be advantageous to prevent damage to a linac using existing cavity structures. It would also be advantageous to provide a more adaptable linac. Accordingly, there is a need for more versatile linacs and linac joints.

The present invention seeks to address these and other disadvantages encountered in the prior art.

SUMMARY

An invention is set out in the independent claims.

According to an aspect, there is provided a reusable joint for a medical linac, the reusable joint comprising a CF choke flange comprising: a first waveguide aperture; a choke groove; and a first CF groove comprising a first knife-edge, wherein the choke groove is disposed radially inwards from the first CF groove on the CF choke flange; a CF cover flange comprising: a second waveguide aperture aligned with the first waveguide aperture; and a second CF groove comprising a second knife-edge and aligned with the first CF groove; and a gasket disposed between and in contact with the first CF groove and the second CF groove.

According to a further aspect, there is provided a reusable CF choke flange for a medical linac, the reusable CF choke flange comprising: a first waveguide aperture; a choke groove; and a first CF groove comprising a first knife-edge, wherein the choke groove is disposed radially inwards from the first CF groove on the reusable CF choke flange.

According to a further aspect, there is provided a linac, the linac comprising: a first linac component; a second linac component; and the above-mentioned reusable joint forming a non-permanent connection between the first linac component and the second linac component.

According to a further aspect, there is provided a method for forming a reusable joint for a medical linac, the method comprising: providing a CF choke flange, the CF choke flange comprising: a first waveguide aperture; a choke groove; and a first CF groove comprising a first knife-edge, wherein the choke groove is disposed radially inwards from the first CF groove on the CF choke flange; providing a CF cover flange, the CF cover flange comprising: a second waveguide aperture aligned with the first waveguide aperture; and a second CF groove comprising a second knife-edge and aligned with the first CF groove; disposing a gasket between and in contact with the first CF groove and the second CF groove; and holding the CF choke flange and the CF cover flange in abutment using attachment means.

FIGURES

Specific embodiments are now described, by way of example only, with reference to the drawings, in which.

DETAILED DESCRIPTION

The current disclosure provides a reusable joint comprising a CF choke flange, a CF cover flange and a gasket. The CF choke flange includes a CF groove located radially outwards from a choke groove. Moving the CF groove to a greater radius, and providing a choke groove at a smaller radius, protects the CF groove and the gasket from damage by travelling RF waves. This ensures that the CF groove and gasket are disposed in a location whereby the electric and magnetic fields are low such that breakdown can be avoided. This enables use of the reusable joint in UHV regions and even in locations where high-power instabilities may occur since the CF groove and gasket are shielded. The reusable joint has the benefit of not requiring brazing or welding, but instead using a combined CF joint and choke joint with attachment means such as a nut and bolt and/or clamps. This enables simplified formation of a joint for a linac and thereby provides more efficient manufacturing and/or servicing of a linac. In addition, these features enable reuse of components to reform a joint and/or to form one or more other joints, thereby providing a more versatile joint.

Figure 1:
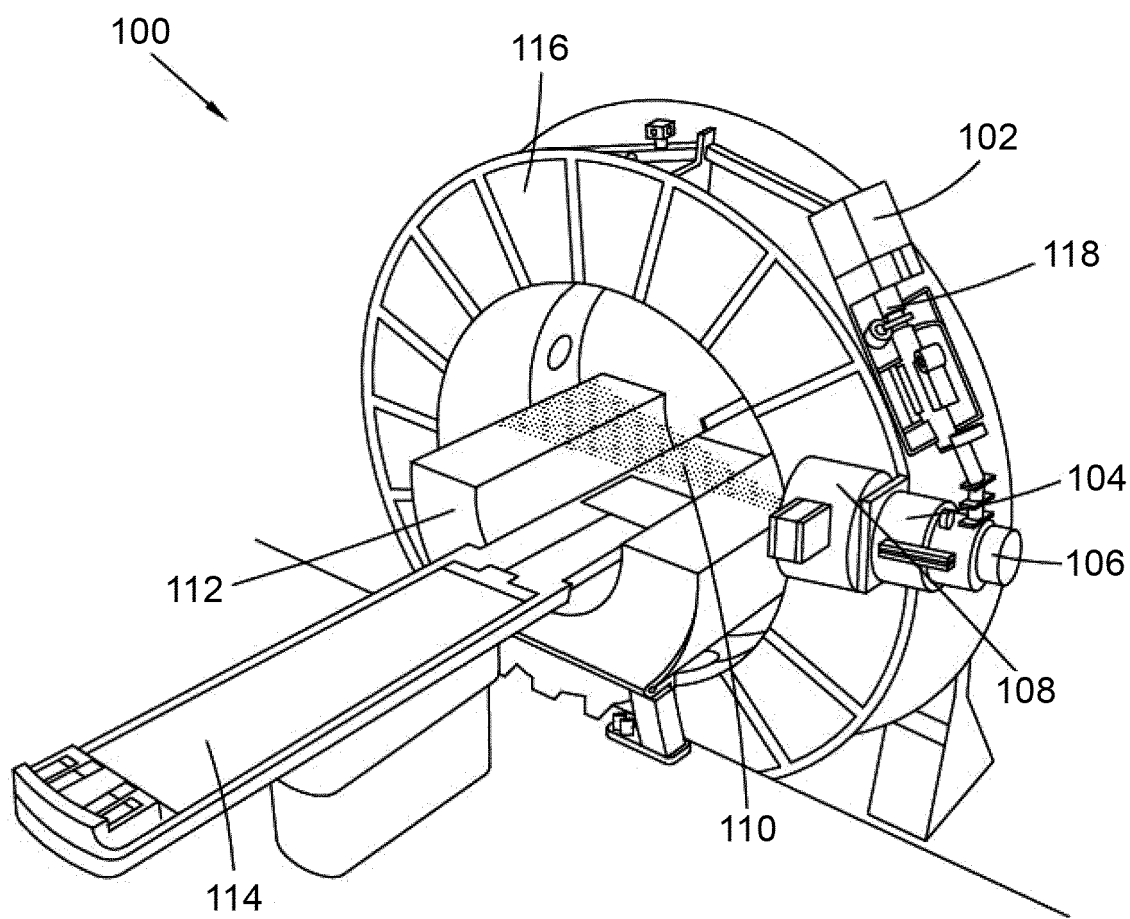
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus; and a subject support surface processor which controls the operation and actuation of the subject support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

The apparatus may be configured to perform any of the method steps presently disclosed and may comprise computer executable instructions which, when executed by a processor, cause a processor to perform any of the method steps presently disclosed. Any of the steps that the apparatus is configured to perform may be considered as method steps of the present disclosure and may be embodied in computer executable instructions for execution by a processor.

In the following, application of radiotherapy to a patient will be referred to in most detail in order to provide clarity of explanation. Such use of the term patient should not be interpreted to limit application of the present disclosure. The present disclosure provides means that can be used to apply radiotherapy to any subject. The terms patient and subject may be used interchangeably herein.

Figure 2:
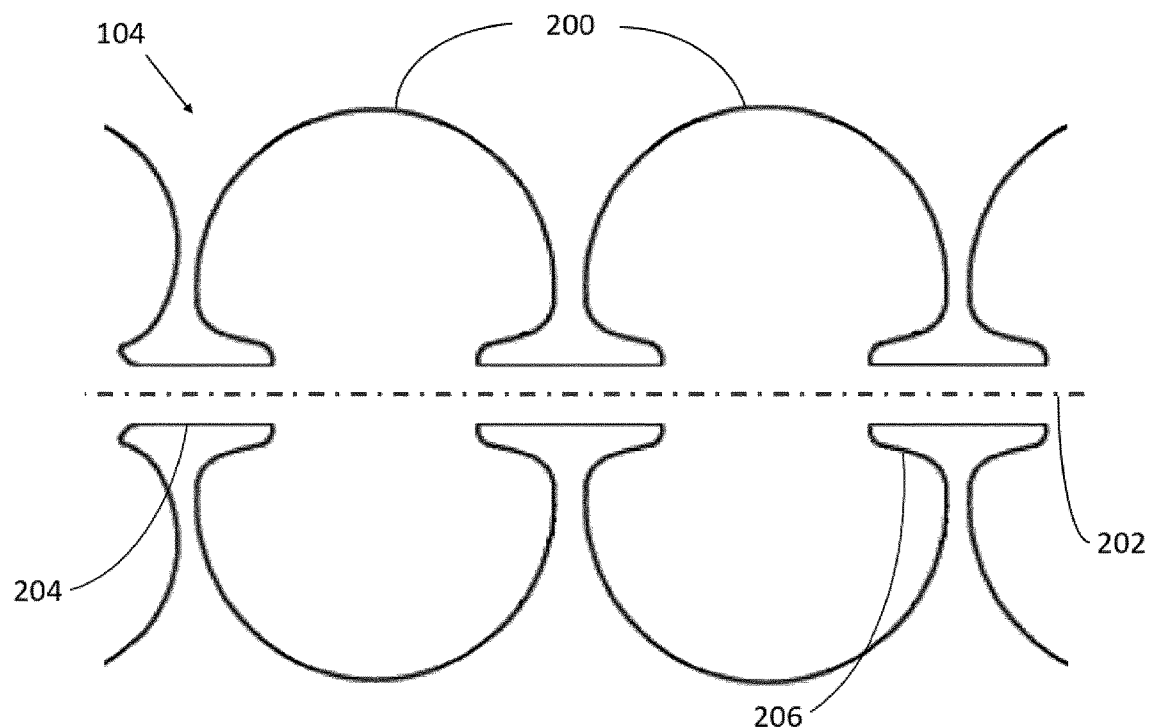
FIG. 2 depicts a waveguide according to the present disclosure.

FIG. 2 depicts a waveguide 104. A cross-sectional view along the longitudinal axis of the waveguide 104 is depicted. This waveguide 104 can be used in the device 100 as shown in FIG. 1, but also could be used in other accelerators (e.g. a curved accelerator such as a cyclotron or a synchrotron). The below examples and discussion relate to the acceleration of electrons, but the waveguide can be used in the acceleration of any charged particle and therefore in any charged particle accelerator. For example, protons, positrons and ions can be accelerated using the techniques described herein.

Two cavities 200 of a series of connected cavities are shown. The cavities are each connected along a central axis 202 by irises 204. Only two cavities are illustrated in FIG. 2, although a typical waveguide will have more. The precise number will vary, dependent on the design criteria of the accelerator. Each cavity is defined in the form of a recess within a surrounding shell of a conductive material, usually copper.

In the following description, the term 'longitudinal cross section' is used to define the cross section in a plane through the centre axis. The 'transverse cross section' is used to define the cross section in a plane orthogonal to the centre axis. A longitudinal centre of an object is the halfway down the object's longitudinal axis. For example, the longitudinal centre of a cavity is the plane half way along the centre axis of that cavity.

The waveguide 104 is designed to accelerate electrons in a longitudinal direction towards a target location. In order to achieve this, the waveguide 104 confines RF waves in transverse directions and conveys the RF waves along the longitudinal direction.

Each cavity 200 has an iris 204 connecting to the preceding cavity 200 in the sequence, and an iris 204 connecting to the next cell in the sequence. The irises 204 and cavities 200 are centred on the centre axis. In use, the central axis 202 defines the electron acceleration path, the path along which electrons travel when being accelerated though the waveguide 104. The cavities 200 and irises 204 may be axisymmetrical around the centre axis, forming a rounded toroid, i.e. the three-dimensional shape created by sweeping a two-dimensional shape around the axis. However, in other arrangements one or more of the cavities 200 may not be axisymmetric around the central axis 202, which may be beneficial for moving the point of peak field away from the respective iris 204.

In the waveguide illustrated in FIG. 2, a 'nose cone' 216 is formed on each end of the iris 204, lengthening the iris 204 along the central axis 202 to protrude into the cavity 200. However, some waveguides 104 do not include a nose cone 206.

In a typical linac, the cavities 200 are manufactured by welding segments of conductive material together at joining portions. The joining portions of the segments are typically in the longitudinal centre of the cavities 200, i.e. at the points of the cavities 200 depicted in FIG. 2 at which the radius of the cavities 200 is greatest.

A joint as described herein can connect two successive cavities 200 in a waveguide 104, for example at the iris 204 between the cavities, or can connect two segments of a cavity 200, for example at a longitudinal centre of the cavity 200. The joints of the present disclosure can also be used to connect other components of the RF system or the linac in general.

The changing electromagnetic field introduced in the waveguide 104 over time through the application of radiofrequency waves can be simulated using a model of the waveguide 104. The effect of the electromagnetic field on an electron, or multiple electrons, injected at one end of the waveguide 104 can be simulated. The acceleration of the electrons along the acceleration path, the speeds of the electron at the far end of the waveguide 104 (the opposing end to the electron gun) and, as some electrons are deflected sideways off the acceleration path, the proportion of electrons reaching the far end of the waveguide 104 can also be determined. In medical applications, this information can be used to determine the dose of radiation created by a waveguide 104.

When RF energy is applied to a waveguide 104, an electric field is created in the waveguide 104, both in the material of the waveguide 104 and within the cavity 200. The electric field is not uniform across the waveguide 104. Surface electric fields are formed on the surface of the cavity 200. Areas with a high surface electric field are more likely to cause electrical breakdown.

Breakdown is caused by a combination of large surface electric and magnetic fields and is a complex phenomenon dependent on many conditional factors in addition to the driving fields. During breakdown the number of electrons reaching the target is typically reduced. In some instances, the number of electrons reaching the target is zeroed.

Figure 3A:
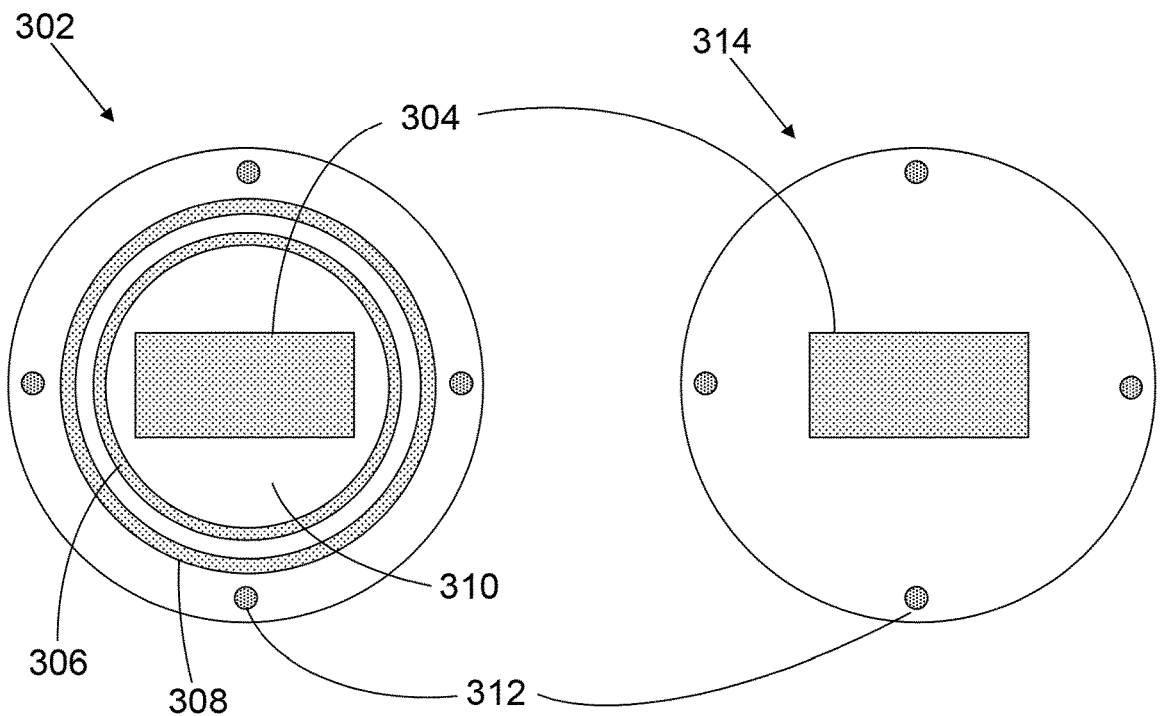
FIG. 3a depicts a longitudinal cross-section of a choke flange and a cover flange.
Figure 3B:
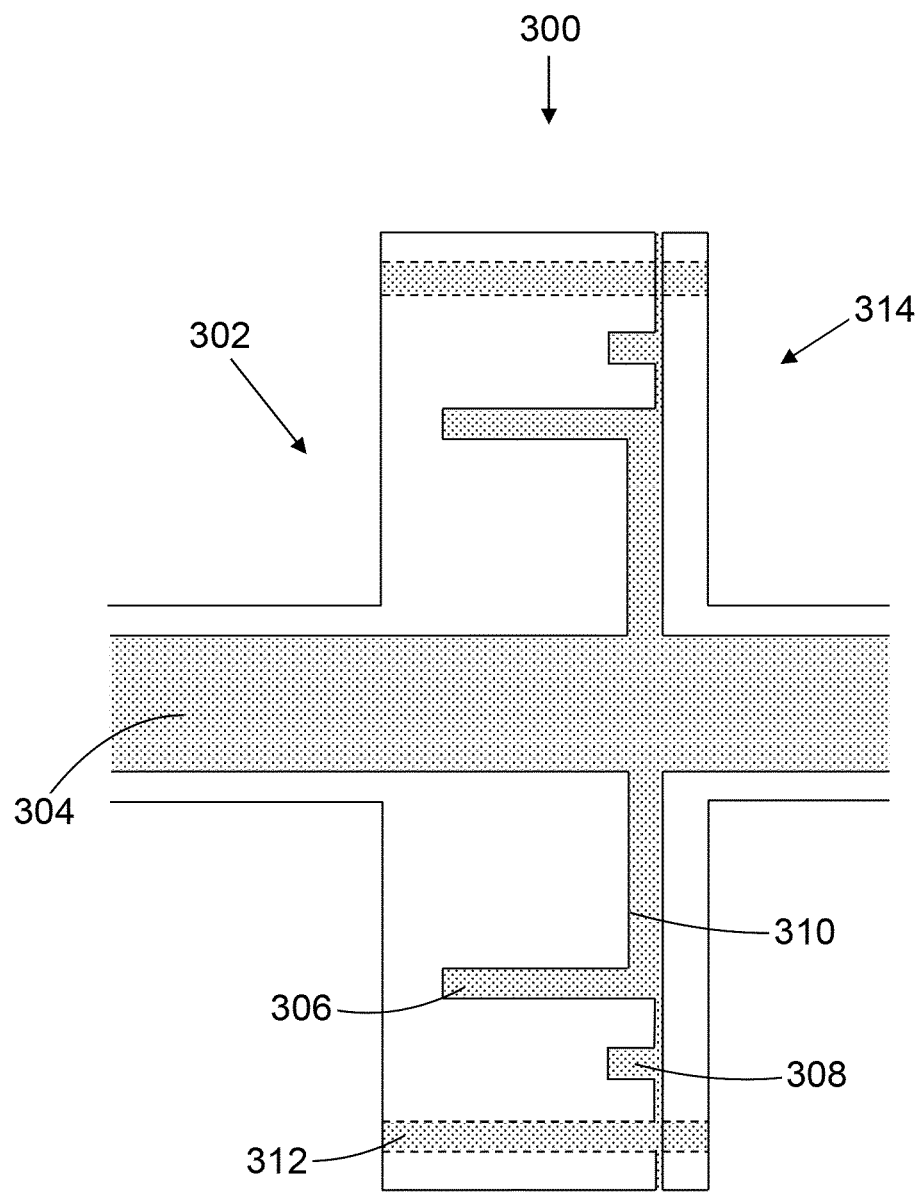
FIG. 3b depicts a transverse cross-section of a choke flange brought into abutment with a cover flange.

FIGS. 3a and 3b depict a choke joint 300, in particular an RF choke joint. FIG. 3a depicts a choke flange 302 (left hand side) and a cover flange 314 (right hand side) face-on, i.e. viewed along their longitudinal axes. FIG. 3b depicts the choke flange 300 and cover flange 314 brought into abutment. Bringing the choke flange 302 into contact with the cover flange 314 and securing the choke flange 302 to the cover flange 314 forms the choke joint 300. The choke flange 302 and the cover flange 314 depicted in FIGS. 3a and 3b have a circular cross-section. However, it will be understood that other cross-sections, such as square and rectangular, are also applicable.

Each of the choke flange 302 and the cover flange 314 comprise a waveguide aperture 304. Depending on the location of the choke joint 300 in the linac, in use, RF waves and/or electrons may pass through the waveguide aperture 304 along the waveguide 104. In addition, each of the choke flange 302 and the cover flange 314 may comprise one or more holes 312. In use, attachment means (not shown) may be combined with the holes 312 to secure the choke flange 302 to the cover flange 314. For example, a bolt (not shown) may be inserted through each hole 312 and a nut (not shown)

fitted to the end of the bolt. Any other suitable attachments means may be used to secure the choke flange 302 to the cover flange 314.

The choke flange 302 comprises a choke groove 306 with a depth extending in the longitudinal direction. The choke groove 306 is annular in shape, and when the choke flange 302 is coupled with the cover flange 314 to form the choke joint, the choke groove 306 forms an annular cavity. The annular groove or cavity is located at a radius larger than the radius of the waveguide aperture 304. The choke groove 306 therefore extends around the waveguide aperture 304 in the plane of the choke flange 302. For example, the depth of the choke groove 306 may extend in a direction parallel to a direction of RF travel, and/or parallel with an outer edge of the choke flange 302.

The region of the cover flange 302 between the waveguide aperture 304 and the choke groove 306 comprises a recess 310. Due to the recess 310, the central part of the choke flange 302 does not contact the cover flange 314 when the outer edges of the faces of the choke flange 302 and the cover flange 314 are brought into contact. Thus, the annular cavity formed by the choke groove 306 and the cover flange 314 is coupled with the waveguide aperture 304 via the recess 310.

For a waveguide 104 configured to convey RF waves of wavelength $\lambda$, the longitudinal depth of the choke groove 306 is typically designed to be $\lambda/4$. As understood by a person skilled in the art, $\lambda$ is related to the operating frequency, or the RF transmission frequency, of the waves conveyed. In addition, the transverse distance between the waveguide aperture 304 and the choke groove 306 is typically designed to be $\lambda/4$.

The choke flange 302 comprises an O-ring groove 308. The O-ring groove 308 is annular in shape, and when the choke flange 302 is coupled with the cover flange 314 to form the choke joint, the O-ring groove 308 forms an annular cavity. The annular cavity formed by the O-ring groove is located at a radius larger than both the radius of the choke groove 306 and the radius of the waveguide aperture 304. The O-ring groove 308 has a depth extending in the longitudinal direction and extends around the choke groove 306 and the waveguide aperture 304 in the plane of the choke flange 302. For example, the O-ring groove 308 may be formed parallel to an outer edge of the choke flange 302 and/or parallel to the choke groove 306. The O-ring groove is configured to house an O-ring used for sealing the choke flange 302 and the cover flange 314 when the attachment means are in operation. The O-ring may be formed from rubber or another suitable elastic or flexible material. In some examples, the cover flange 314 may also comprise an O-ring groove.

In use, electric current flows along the interior surface of the waveguide 104. Therefore, at a waveguide joint, this current must be able to cross the joint without significant reflection or loss. In other words, when the choke flange 302 and the cover flange 314 are brought into contact, electromagnetic continuity must be provided between the choke flange 302 and the cover flange 314 such that RF waves of the desired frequency can travel along the waveguide 104. For current flowing longitudinally along the waveguide aperture 304, the recess 310 and the choke groove 306 together form a side branch to the waveguide aperture 104. This side branch presents a low impedance at the junction between this side branch and the waveguide aperture 304. This surface current flows along the waveguide aperture 304 and recess formed by 310 and 314 when joined. In contrast, at the outer edges of the side branch, i.e. where the choke flange 302 physically contacts the cover flange 314 when they are brought into contact, a high impedance is presented. This limits the current flowing through this point and thereby reduces the risk of arcing between the choke flange 302 and the cover flange 314. Since the depth of the choke groove 306 is typically designed to be $\lambda/4$, this choke groove 306 comprises a quarter-wave resonant short-circuit stub which provides high impedance where it meets the channel formed by the recess 310. Similarly, since the transverse distance between the waveguide aperture 304 and the choke groove 306 is typically designed to be $\lambda/4$, the channel formed by the recess 310 comprises a quarter-wave transformer, which transforms the high impedance at the connection with the choke groove 306 to the low impedance at the connection with the waveguide aperture 304.

Figure 4:
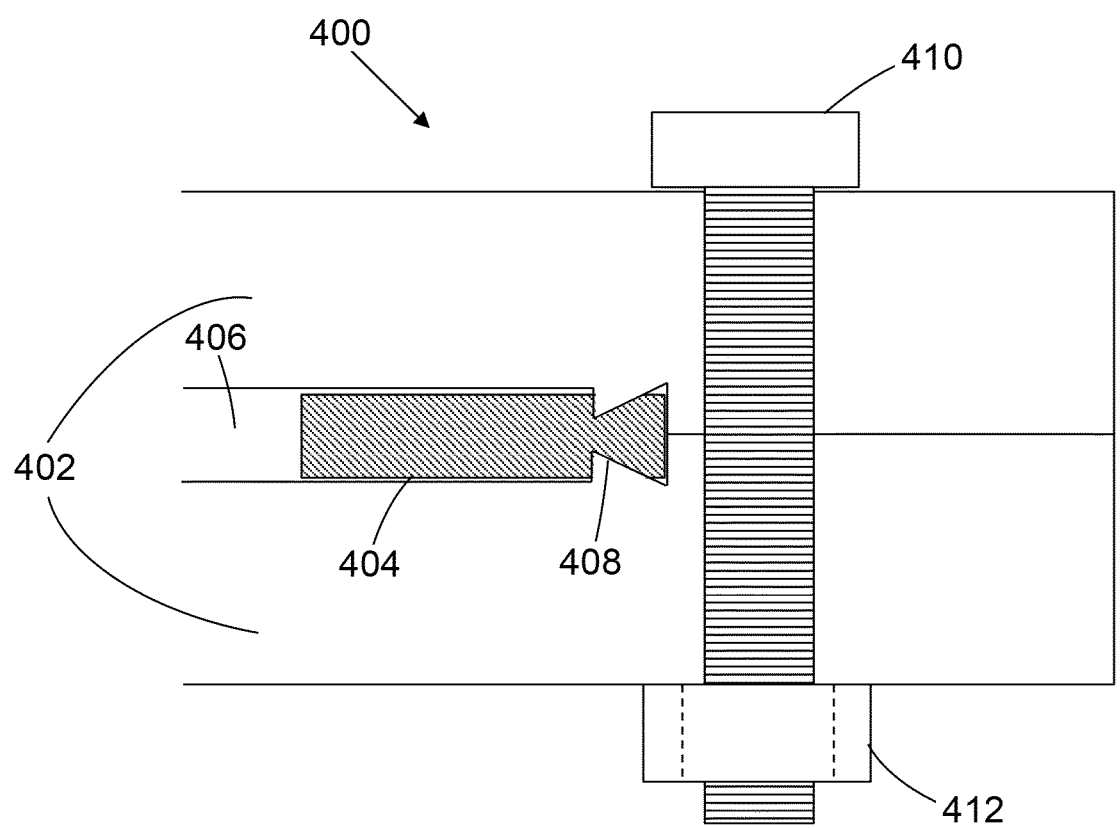
FIG. 4 depicts a cross-section of a CF joint.

FIG. 4 depicts a cross-section of a CF joint 400. The CF joint 400 comprises first and second flanges 402 and a gasket 404. The gasket 404 is disposed in a gap, i.e. a recess or a cavity, between the first and second flanges 402. Inboard of the gasket 404 (to the left of FIG. 4) is a vacuum 406 (e.g. part of an interior of a waveguide 104). The first and second flanges may be brought into contact and forced together via a bolt 410 and a nut 412. Other attachment or forcing means may be used to force the first and second flanges 402 together. Each of the first and second flanges 402 comprises a knife-edge 408 protruding into the gap between the first and second flanges 402. Each of the knife edges 408 may be described as a protrusion, for example a triangular protrusion, or a ridge.

In use, via tightening of the nut 412 on the bolt 410, or via other forcing means, the knife-edges 408 protrude into the gasket 404. The flanges 402, or at least the knife edges 408, are formed from a harder material (for example stainless steel or surface hardened aluminium) than the gasket 404 (which may be formed from copper). The knife-edges 408 deform the gasket 404 such that it extrudes to fill defects in the surface of the gap formed between the flanges 402, forming a seal between the flanges 402.

RF chokes as shown in FIGS. 3a and 3b cannot be used in UHV regions since they use an O-ring seal and tend to lead to arcs when the VSWR is swung too far. CF joints as shown in FIG. 4 are vulnerable to being damaged (e.g. burned) by RF waves as these waves pass along a waveguide. Therefore, there is a need for a joint that addresses these problems.

Figure 5:
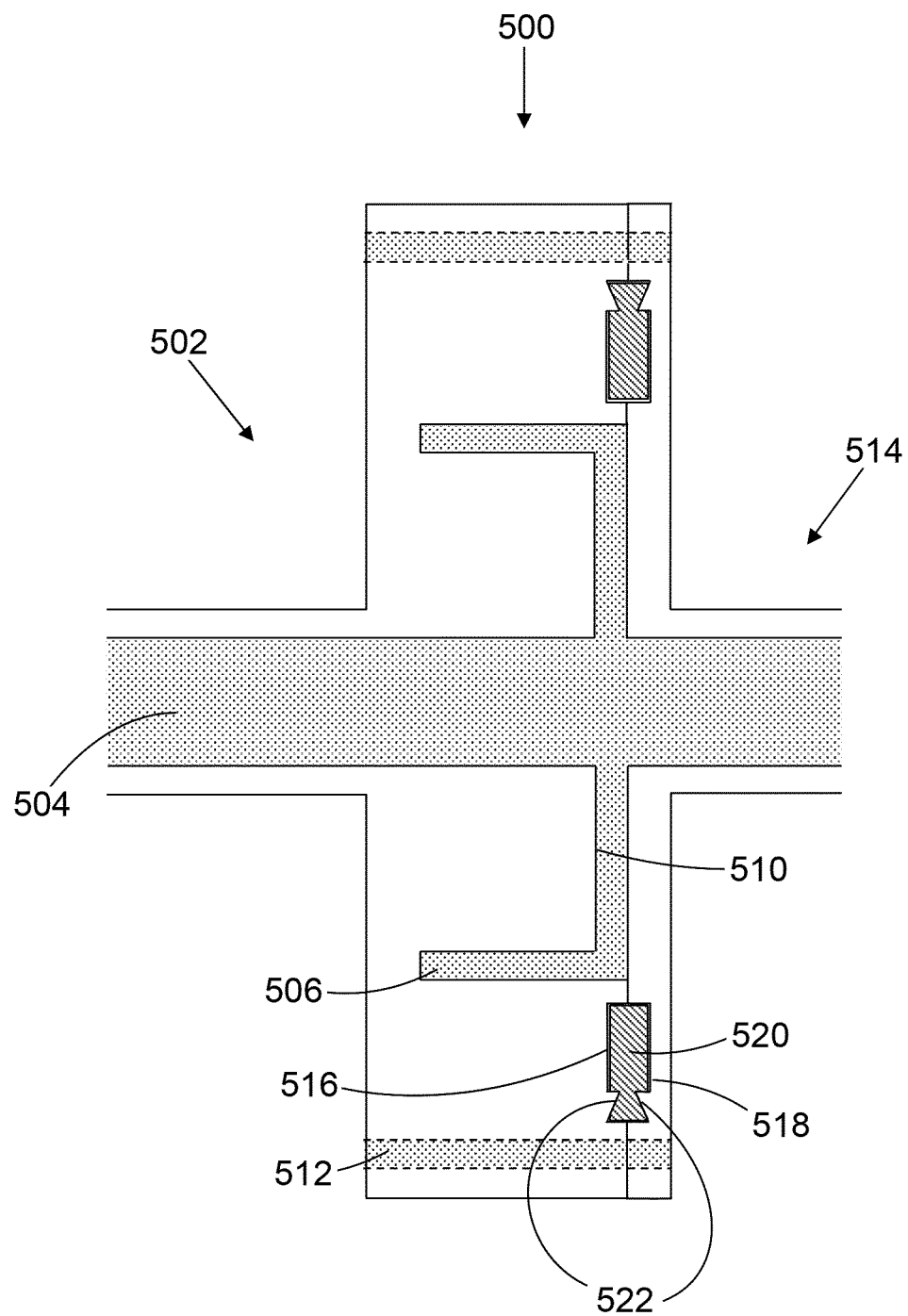
FIG. 5 depicts a transverse cross-section of a CF choke joint according to the present disclosure.

FIG. 5 depicts a transverse cross-section of a CF choke joint 500 according to the present disclosure and comprising a CF choke flange 502 and a CF cover flange 514. The CF choke flange 502 and the CF cover flange 514 each comprise a waveguide aperture 504 and may each comprise holes 512 suitable for receiving attachment means (not shown). The CF choke flange comprises a choke groove 506 and a recess 510. The waveguide aperture 504, holes 512, attachment means, choke groove 506 and/or recess 510 may correspond to or be similar to those described in relation to FIG. 3a and FIG. 3b. As used herein, a reference to a waveguide aperture may be considered to be a reference to any component which is configured to allow a beam of particles and/or radiation to pass therethrough. As used herein, a reference to a waveguide aperture may be considered to be a reference to an RF transition.

The CF choke flange 502 comprises a first CF groove 516. The CF cover flange 514 comprises a second CF groove 518. Each of the first CF groove 516 and the second CF groove 518 comprises a knife-edge 522. A gasket 520 is disposed between the first CF groove 516 and the second CF groove 518.

The waveguide aperture 504 of the CF choke flange 502 may be aligned with the waveguide aperture 504 of the CF cover flange 514 when the CF choke flange 502 and the CF cover flange 514 are brought into abutment. The first CF groove 516 may be aligned with the second CF groove 518 when the CF choke flange 502 and the CF cover flange 514 are brought into abutment. The knife edge 522 of the CF choke flange 502 may be aligned with the knife edge 522 of the CF cover flange 514 when the CF choke flange 502 and the CF cover flange 514 are brought into abutment. The holes 512 of the CF choke flange 502 may be aligned with the holes 512 of the CF cover flange 514 when the CF choke flange 502 and the CF cover flange 514 are brought into abutment.

The holes 512 may be disposed in a longitudinal direction through each of the CF choke flange 502 and the CF cover flange 514. In some examples, interior walls of the holes 512 may be threaded to receive a bolt with corresponding threading. In other examples, the interior walls of the holes may be smooth or flat in a longitudinal direction. Attachment means or forcing means may be provided in the holes 512. For example, the attachment means or forcing means may comprise a bolt and a nut. When a nut is tightened on a bolt disposed through one or more of the holes 512, the knife edges 522 deform the gasket 520 such that it extrudes to fill defects in the surfaces of the CF choke flange 502 and the CF cover flange 514, thereby forming a seal between the CF choke flange 502 and the CF cover flange 514. Alternatively, or in addition, the attachment or forcing means may comprise one or more clamps. The CF choke flange 502 and the CF cover flange 514 may be held in abutment by one or more of these clamps and forced together such that the gasket 520 is deformed by the knife edges 522 in a similar manner to that described above. These attachment or forcing means enable uniform deformation of the gasket 520, which is beneficial for forming a reliable seal.

FIG. 5 may depict a transverse cross-section through a CF choke joint 500 with a circular longitudinal cross-section. In other words, one or more of the choke groove 506, the first CF groove 516, the second CF groove 518, the knife edges 522 and the gasket 520 may be circular, i.e. annular, in shape.

As depicted in FIG. 5, relative to the centre of the CF choke flange 502, the choke groove 506 is at a greater radius than the waveguide aperture 504. The first CF groove 516, the second CF groove 518, the gasket 520 and the knife-edges 522 are at a greater radius than the choke groove 506. Moving these components to greater radii, and providing a choke groove 506 at a smaller radius, protects these components from damage by travelling RF waves. This ensures that the CF joint is disposed in a location whereby the electric and magnetic fields are low such that breakdown can be avoided. This enables use of the waveguide joint in UHV regions and even in locations where high-power instabilities may occur since the CF joint is shielded.

The CF choke joint 500 can be used at interfaces in vacuum RF systems. For example, the CF choke joint 500 can be used in linacs (e.g. medical linacs) or other such RF systems in which there exists high power and a range of frequencies across a potentially wide range of VSWR values. While this joint has been discussed in terms of a waveguide, the joint can also be applied to various parts of a linac. The joint may be suitable for use in a medical linac such as for delivery of radiotherapy. For example, the joint may be applied to an interface between a target section and the linac, an electron gun/particle source and the linac, an RF window and the linac, and between cavities or sections of cavities within the linac. These interfaces are traditionally brazed or welded. Such brazed or welded interfaces are considered non-serviceable options for a medical linac since repair or alteration requires substantial reworking at a factory/place of manufacture rather than allowing for onsite repair.

The CF choke joint 500 can be formed without requiring brazing or welding. Instead, attachment means can be used to form the CF choke joint 500 by holding the CF choke flange 502 and the CF cover flange 514 in abutment. For example, the attachment means may comprise a bolt disposed through each of holes 512. A nut may be fastened on the bolt so as to force the CF choke flange 502 against the CF cover flange 514. The CF choke joint 500 is reusable. In other words, the CF choke flange 502 and CF cover flange 514 may be separably coupled to each other and may enable subsequent recouplings. In other words, the CF choke flange 502 and the CF cover flange 514 may be separated and each reused to reform the same joint or to form one or more other joints with other linac components. A new gasket 520 may be used to reform the same joint or to form another joint. The present disclosure also comprises a method for forming a reusable joint for a medical linac according to the means described above.

For example, the nut may be uncoupled from the bolt such that the CF choke flange 502 may be disassociated from the CF cover flange 514. Alternatively, or in addition, the CF choke flange 502 may be disassociated from the CF cover flange 514 by removing one or more clamps from the CF choke flange 502 and the CF cover flange 514.

The CF choke joint 500 has the benefit of not requiring brazing or welding, but instead using a combined CF joint and choke joint with attachment means such as a nut and bolt and/or clamps. This enables simplified formation of a joint for a linac and thereby provides more efficient manufacturing and/or servicing of a linac. In addition, these features enable reuse of components to reform a joint and/or to form one or more other joints, thereby providing a more versatile joint.

The present disclosure comprises a linac comprising the reusable joint, which enables one or more linac components to be removed, replaced and/or repaired, for example removed, replaced and/or repaired onsite. This has the benefit of allowing full onsite serviceability, enabling replacement of damaged or failed components such as the target, electron gun or RF window. Such a linac may be referred to as a modular linac. The linac may comprise a medical device, for example a radiotherapy device configured to apply radiation to a subject.

A further benefit of the present disclosure is that a waveguide/linac can be upgraded retroactively based on changes in desired use or available resources. For example, a larger relativistic section could be provided by adding further waveguide cavities. Alternatively, or in addition, increased functionality could be provided by adding an energy switch, different targets and/or different particle sources to a linac. Therefore, the waveguide/linac provides increased versatility and flexibility.

The linac may comprise a plurality of components with joints therebetween. At least one of the joints may be a CF choke joint 500. In other words, at least one of the joints may be formed by connecting a CF choke flange 502 with a CF cover flange 514 as described in relation to FIG. 5.

This modular design does not have issues of creep and detuning caused by using an Indium seal joint design with a soft Indium metal.

Design of a joint as discussed herein may be dependent on the intended location of the joint within a waveguide or linac and the intended power, intended range of frequencies and likely VSWR values. Design of the joint may comprise simulation of the joint, in particular of the electric and magnetic fields. The design of the joint may be optimised for an input set of conditions such that: the power reflected at the joint is minimised; there are no trapped RF modes in the region of interest; and the electric and magnetic fields are below a threshold value within the region of the CF joint (to prevent damage from RF breakdown, surface current effects and other field-related phenomena). The design of the joint may minimise the fields across the joint for particular space constraints. A candidate design of the joint may be checked to ensure it is suitable for expected power levels, for example using multipacting and/or Townsend's runaway condition. Therefore, the joint may be designed for a particular space and power constraint. The joint may also be designed to accommodate limits or tolerances of machining or manufacture.

Specific embodiments of CF choke joints according to the present disclosure are set out below.

Figure 6A:
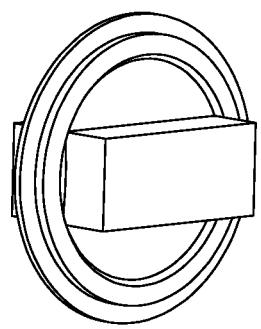
FIG. 6a depicts a perspective view of a CF choke joint according to the present disclosure.
Figure 6B:
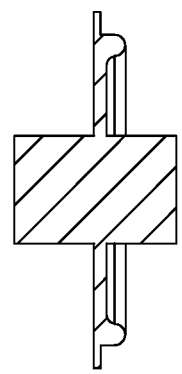
FIG. 6b depicts a transverse cross-section of a CF choke joint according to the present disclosure.
Figure 6C:
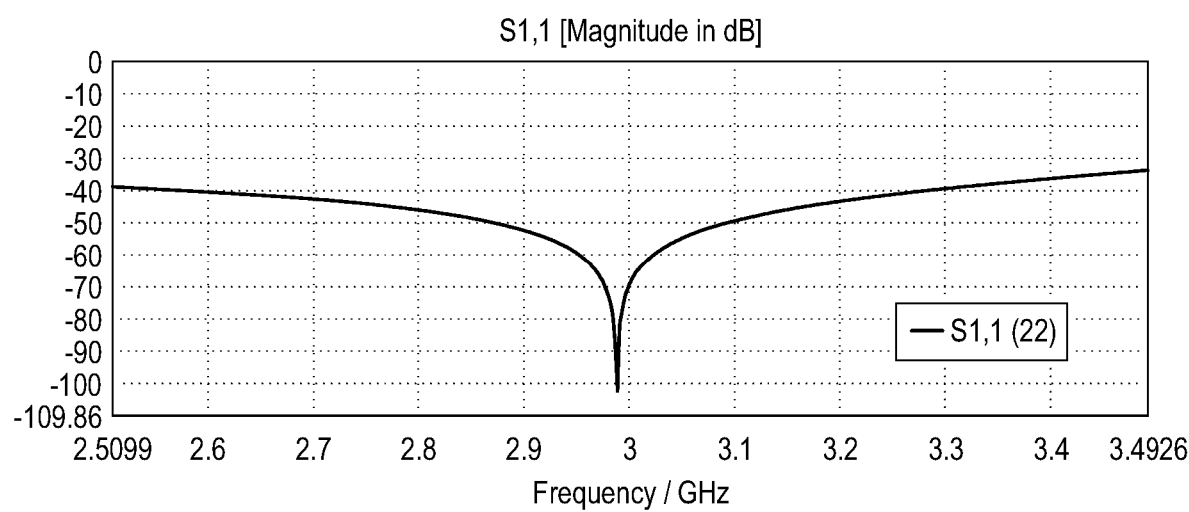
FIG. 6c depicts a simulated broadband response of a CF choke joint according to the present disclosure.

FIG. 6a depicts a perspective view of an embodiment of a CF choke joint. FIG. 6b depicts a transverse cross-section of this CF choke joint. These figures depict the spaces between and around the relevant physical components of the CF choke joint. FIG. 6c depicts a simulated broadband response of the CF choke joint in the worst-case scenario of setting a ¼ wavelength condition. Setting a ¼ wavelength condition gives the worst case scenario because the field will be at a maximum under this condition. In other words, FIG. 6c depicts a magnitude of the response in decibels for a swept range of frequencies. As can be seen from FIG. 6c, the joint is designed to be at a null position at resonance f0=2.998 GHz. As the frequency is moved away from this null the response rises. However, for this particular design, within f0±10 MHz beneficially the power is still very low, i.e. below −60 dB.

Figure 7A:
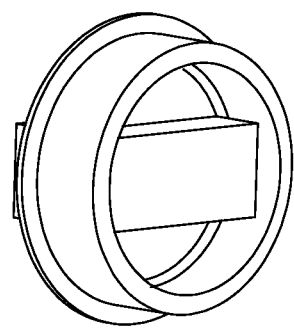
FIG. 7a depicts a perspective view of an alternative CF choke joint according to the present disclosure.
Figure 7B:
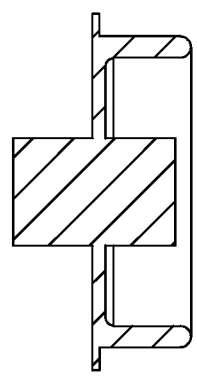
FIG. 7b depicts a transverse cross-section of an alternative CF choke joint according to the present disclosure.

FIG. 7a depicts a perspective view of an alternative embodiment of a CF choke joint. FIG. 7b depicts a transverse cross-section of this CF choke joint. These figures depict the spaces between and around the relevant physical components of the CF choke joint. Variants on the design of the CF choke joint are dependent upon design constraints such as space, frequency range and the expected VSWR range that the system can expect to see. The embodiment depicted in FIGS. 7a and 7b may therefore be designed for a different system application or location to the embodiment depicted in FIGS. 6a and 6b. As shown in FIGS. 7a and 7b, this embodiment has an extended choke groove relative to FIGS. 6a and 6b. The embodiment depicted in FIGS. 6a and 6b may be easier to make than that depicted in FIGS. 7a and 7b, for example based on tolerancing and machinability. However, the overall dimensions of the embodiment depicted in FIGS. 6a and 6b may be much larger than that depicted in FIGS. 7a and 7b and therefore it may be difficult to source off the shelf gaskets and knife edges/flanges for the embodiment depicted in FIGS. 6a and 6b. The choice of design involves a balance between practicality and sourcing. If there are space restrictions in the intended location of the joint then the embodiment of FIGS. 7a and 7b may be used instead of the embodiment of FIGS. 6a and 6b.

Figure 7C:
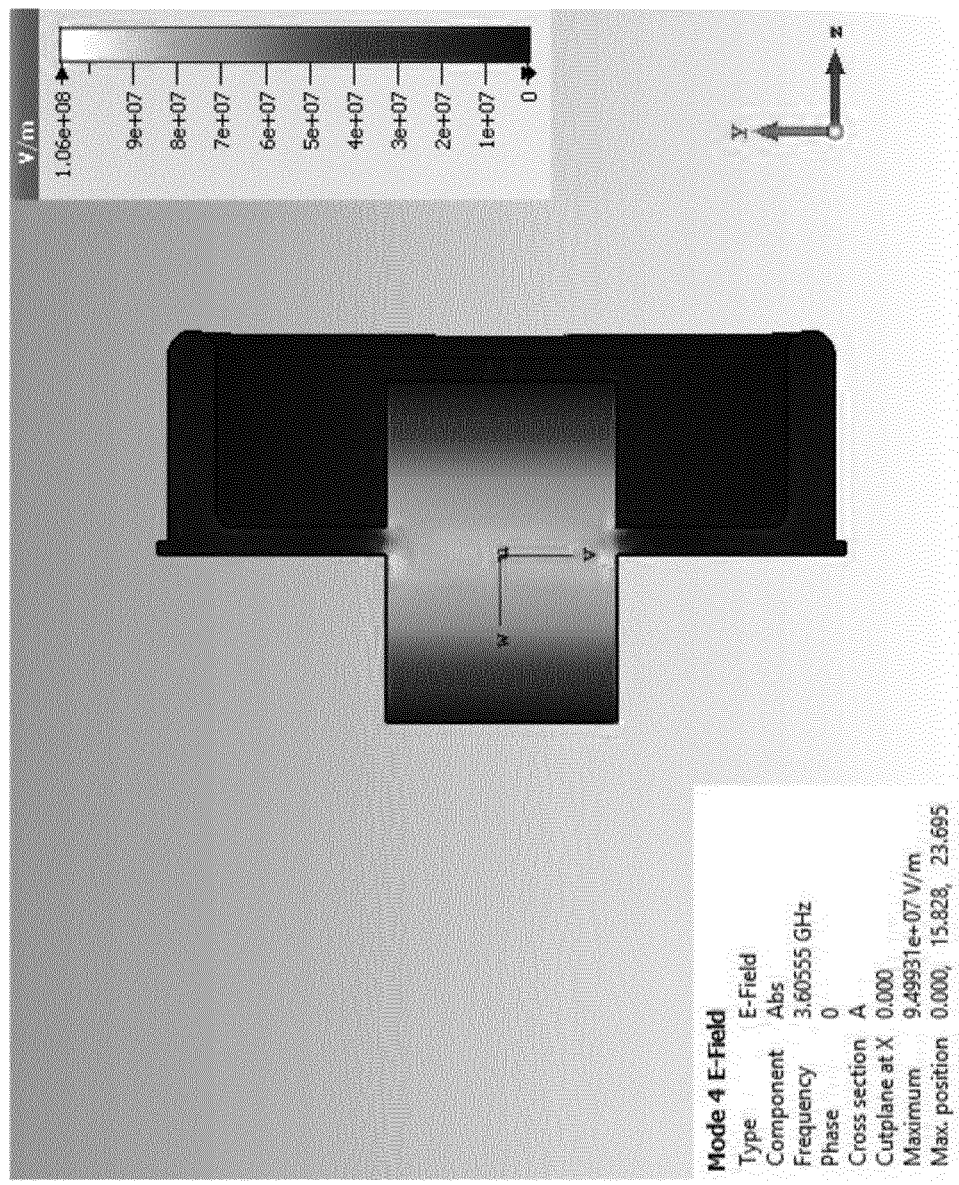
FIG. 7c depicts a simulation of the electric field present in a CF choke joint according to the present disclosure.
Figure 7D:
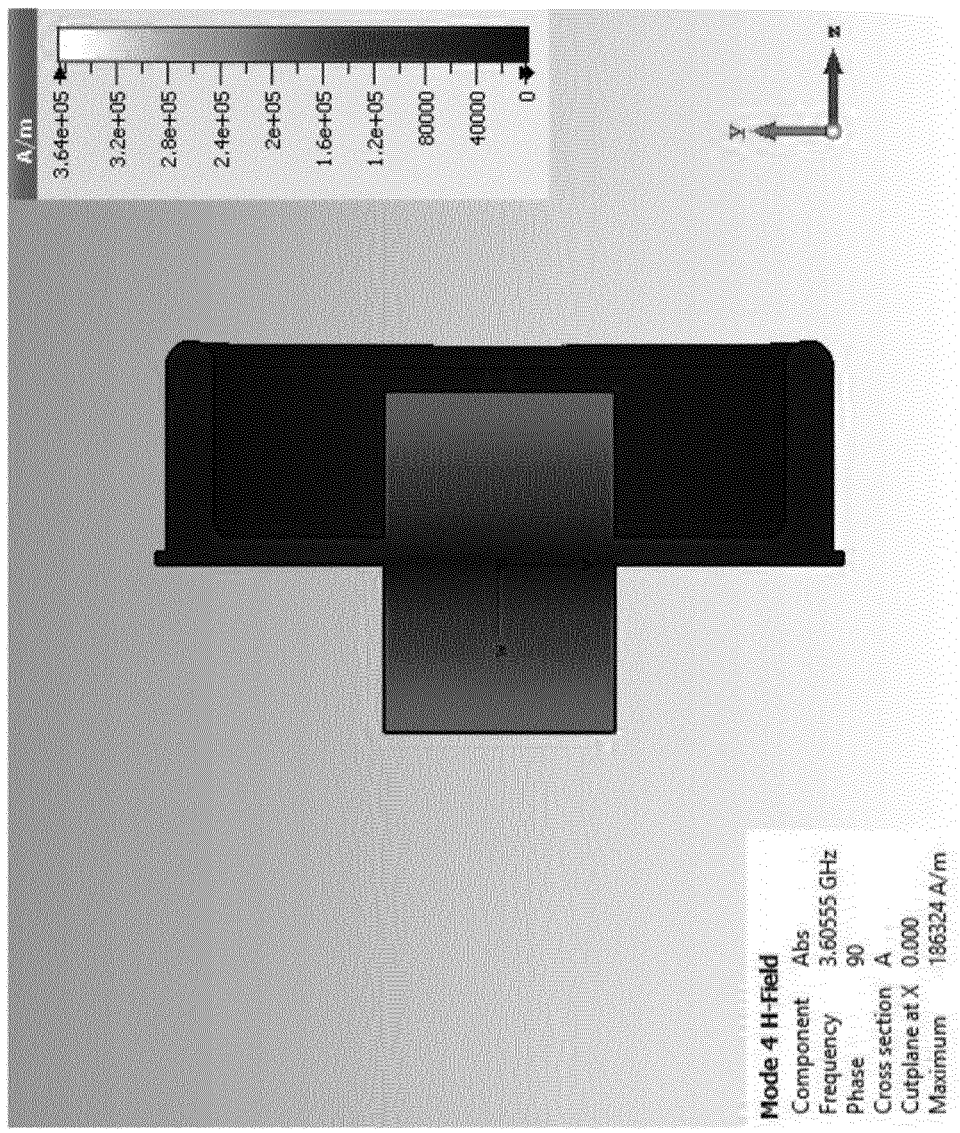
FIG. 7d depicts a simulation of the magnetic field present in a CF choke joint according to the present disclosure.

FIG. 7c depicts a simulation of the electric field present in the CF choke joint of FIGS. 7a and 7b in use. Similarly, FIG. 7d depicts a simulation of the magnetic field present in the CF choke joint of FIGS. 7a and 7b in use. These Figures depict the fields present in the spaces between and around the relevant physical components of the CF choke joint. As shown in FIGS. 7c and 7d, both the electric and magnetic fields are minimised towards the outer radial surface of the CF choke joint (towards the top and bottom of each of the Figures), i.e. at the location of the CF joint. FIG. 7c depicts a high electric field in the centre of the simulation along a horizontal axis. The electric field decreases away from the centre towards both the left and the right sides of the simulation. FIG. 7d depicts a low magnetic field in the centre of the simulation along a horizontal axis. The magnetic field increases away from the centre towards both the left and the right sides of the simulation.

While the above embodiments have a circular geometry, the CF choke joint and the CF choke flange are not limited to this, but can take any shape appropriate for the particular design application. For example, the choke joint and/or the CF joint can be circular, square, rectangular, elliptical or a spline variant. The design of the choke joint and/or the CF joint is limited by the design process to meet the aforementioned requirements of minimal electric and surface fields across the joint and absence of trapped modes.

Figure 8A:
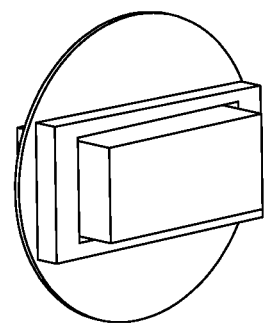
FIG. 8a depicts a perspective view of an alternative CF choke joint according to the present disclosure.
Figure 8B:
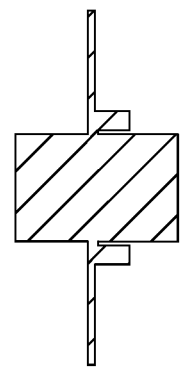
FIG. 8b depicts a transverse cross-section of an alternative CF choke joint according to the present disclosure.
Figure 8C:
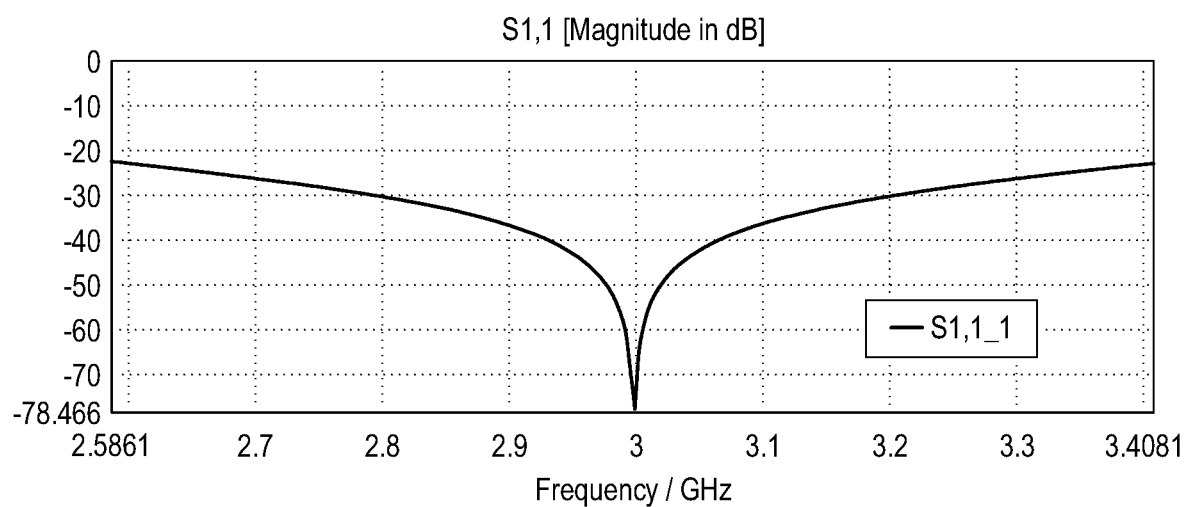
FIG. 8c depicts a simulated broadband response of an alternative CF choke joint according to the present disclosure.

FIG. 8a depicts a perspective view of a further alternative embodiment of a CF choke joint with a rectangular geometry. FIG. 8b depicts a transverse cross-section of this CF choke joint. These figures depict the spaces between and around the relevant physical components of the CF choke joint. FIG. 8c depicts a simulated broadband response of this CF choke joint in the worst-case scenario of setting a ¼ wavelength condition. In other words, FIG. 8c depicts a magnitude of the response in decibels for a swept range of frequencies.

While the embodiments described above relate to a CF choke joint comprising a single jointed section, the disclosure is not limited thereto. The CF choke joint is extendable to any number of jointed sections, including double and triple jointed sections. Such embodiments may include different matching regions and/or different flange types, in which case the different sections can be matched to each other via the CF choke joint. This may be of benefit, for example, for connecting two dissimilar or mismatching sections of the RF system, for example with different shapes and/or diameters.

Figure 9A:
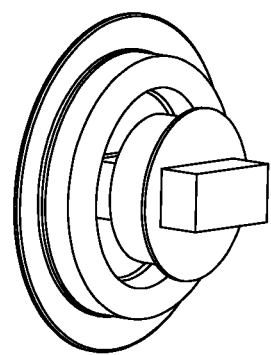
FIG. 9a depicts a perspective view of an alternative CF choke joint according to the present disclosure.
Figure 9B:
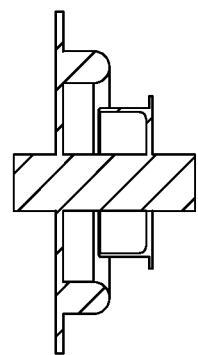
FIG. 9b depicts a transverse cross-section of an alternative CF choke joint according to the present disclosure.

FIG. 9a depicts a perspective view of a further alternative embodiment of a CF choke joint in which two CF choke joints are combined (interleaved). In other words, the CF choke joint of FIG. 9a comprises two chokes and may also comprise two CF joints. FIG. 9b depicts a transverse cross-section of this CF choke joint. This CF choke joint may be used to join/connect different flange types in an RF waveguide system. These figures depict the spaces between and around the relevant physical components of the CF choke joint.

As described above, the CF choke joints described herein can be applied to various different sections of a UHV RF system. Non-limiting examples of possible applications are described below.

Figure 10:
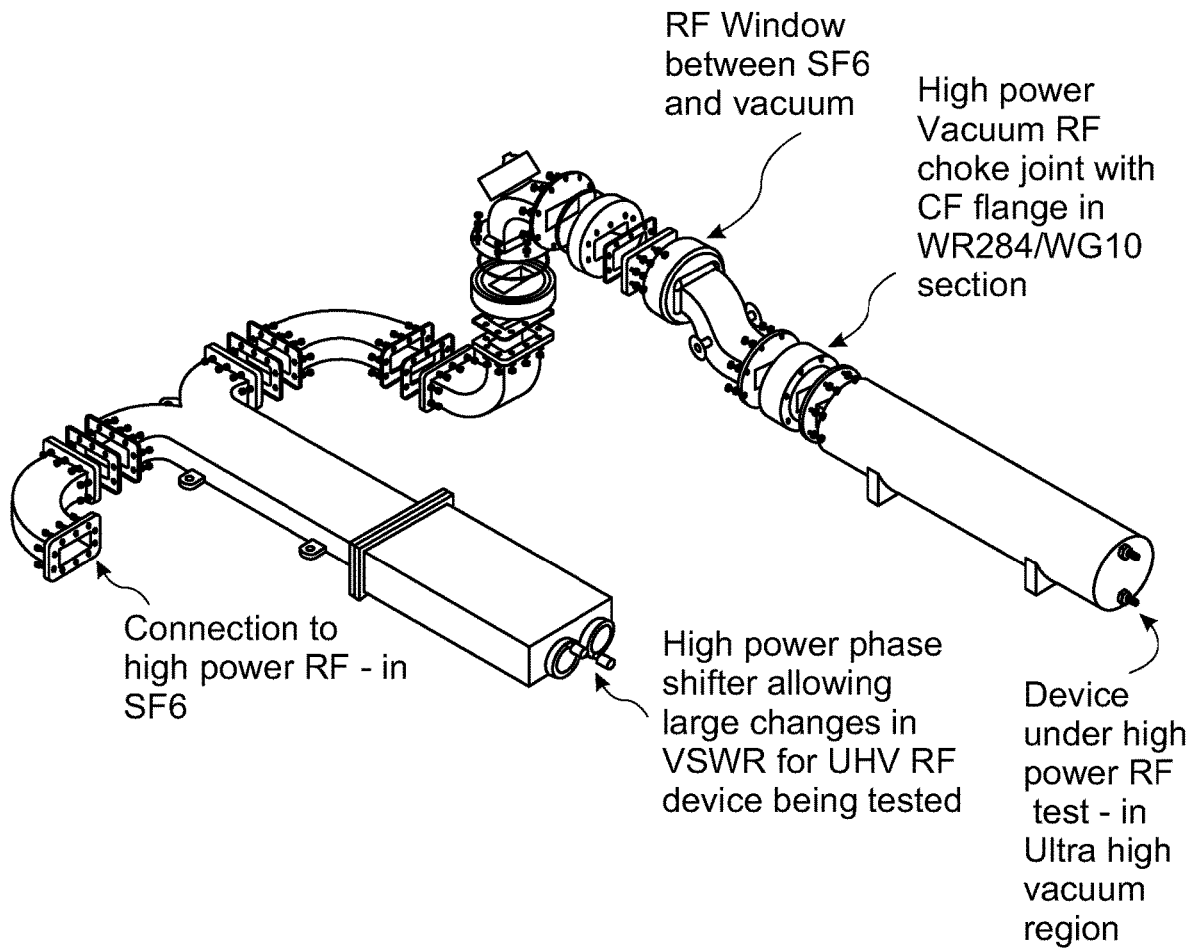
FIG. 10 depicts a UHV RF system according to the present disclosure.

FIG. 10 depicts an example of a UHV RF system including a connection to high power RF, an RF window, a device under test and a high-power phase shifter. The UHV RF system depicted may have a large VSWR range of 1-6. A CF choke joint can be applied, for example, at the intersection between a region of high-power RF and a UHV region.

The CF choke joint described herein can be applied not only to RF waveguide transport systems (such as WR284/WG10 for example), but also to various parts of a linac. For example, the CF choke joint can be applied to interfaces that are traditionally brazed and welded. As non-limiting examples, these interfaces may be between: the target section and the linac; the electron gun/particle source and the linac; the RF window and the linac; and/or the waveguide cavities or sections of the waveguide cavities within the linac.

Figure 11A:
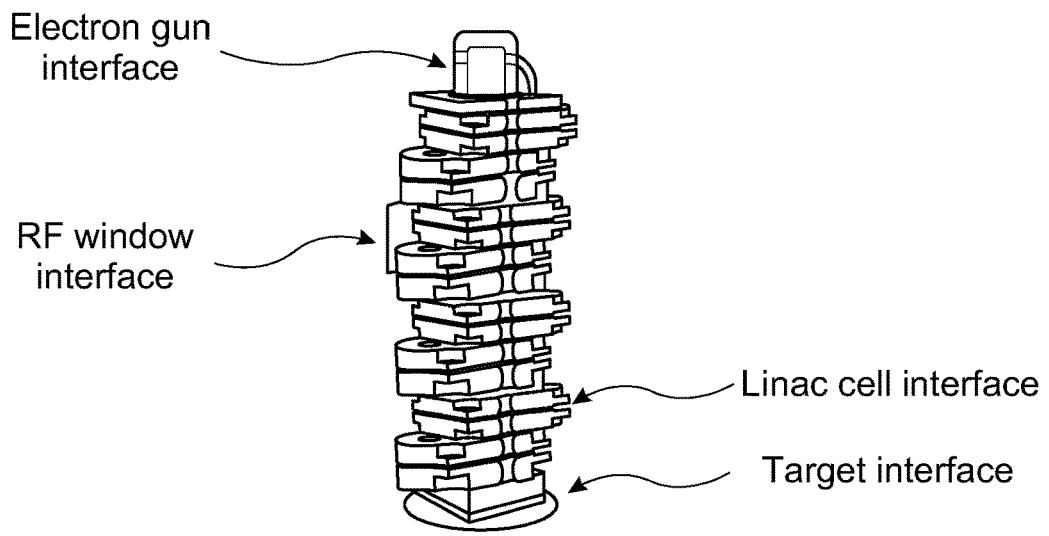
FIG. 11a depicts a medical linac according to the present disclosure.
Figure 11B:
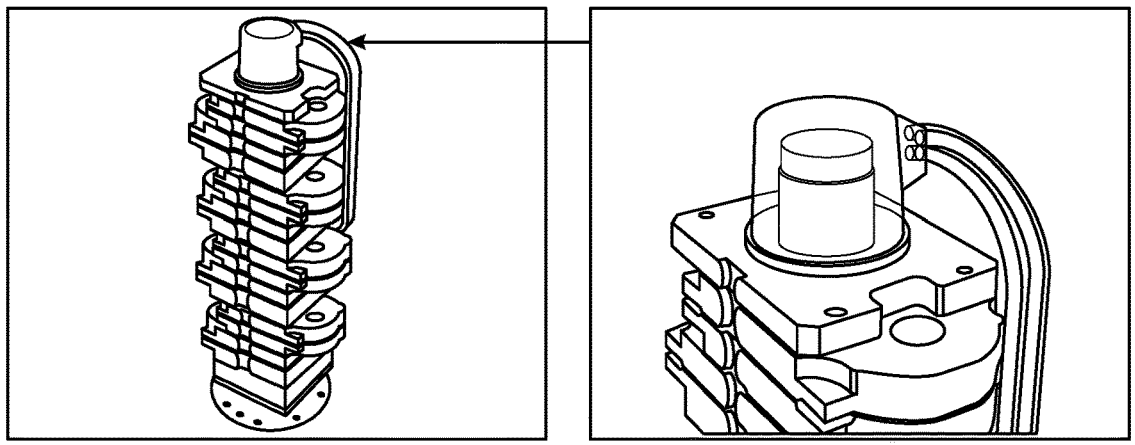
FIG. 11b depicts an expanded view of an electron gun interface according to the present disclosure.
Figure 11C:
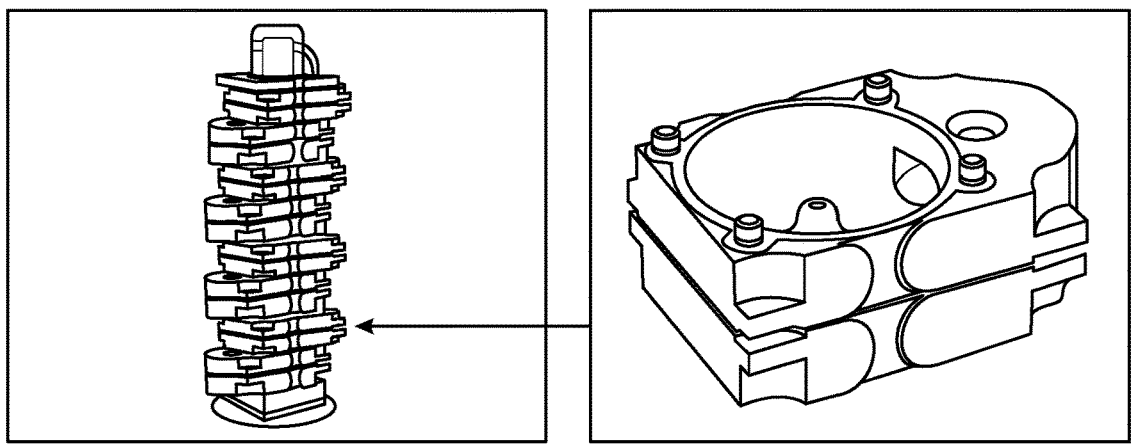
FIG. 11c depicts an expanded view of linac cells according to the present disclosure.

FIG. 11a depicts an example of a medical linac including an electron gun interface, a target interface, a linac cell interface and an RF window interface. FIG. 11b depicts an expanded view of the electron gun interface. FIG. 11c depicts an expanded view of the linac cell interface. The interfaces depicted in these Figures are traditionally brazed or welded. However, these interfaces can instead by joined using the CF choke joint described herein. This provides a modular, more versatile and more flexible medical linac.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A reusable ConFlat (CF) joint for a medical linear accelerator (linac), the reusable CF joint comprising:
   a CF choke flange comprising:
      a choke groove; and
      a first CF groove comprising a first knife-edge, wherein the choke groove is disposed radially inwards from the first CF groove on the CF choke flange;
   a CF cover flange comprising:
      a second CF groove comprising a second knife-edge and aligned with the first CF groove; and
      a gasket disposed between and in contact with the first CF groove and the second CF groove;
   wherein the CF choke flange and the CF cover flange comprise a waveguide aperture configured to allow passage of at least one of RF waves or electrons through the waveguide aperture along a waveguide.

2. The reusable CF joint according to claim 1, wherein the CF choke flange and the CF cover flange are held in abutment by an attachment member.

3. The reusable CF joint according to claim 2, wherein the CF choke flange and the CF cover flange each comprise one or more holes disposed therethrough, wherein the attachment member comprises one or more bolts and one or more nuts, wherein the one or more bolts are disposed through respective holes of the CF choke flange and the CF cover flange, wherein a respective one of the one or more nuts are coupled to a respective one of the one or more bolts to hold the CF choke flange and the CF cover flange in abutment, and wherein the CF choke flange and the CF cover flange are separably coupled to enable separation thereof by uncoupling the one or more nuts from the one or more bolts.

4. The reusable CF joint according to claim 2, wherein the attachment member comprises one or more clamps arranged to hold the CF choke flange and the CF cover flange in abutment, wherein the CF choke flange and the CF cover flange are separably coupled to enable separation thereof by removing the one or more clamps from the CF choke flange and the CF cover flange.

5. The reusable CF joint according to claim 1, wherein the CF choke flange and the CF cover flange are not brazed or welded together.

6. The reusable CF joint according to claim 1, wherein the CF choke flange and the CF cover flange have a circular cross-section, or wherein the CF choke flange and the CF cover flange have a square or rectangular cross-section.

7. The reusable CF joint according to claim 1, wherein a plurality of reusable CF joints each according claim 1 are combined or interleaved to form a plurality of jointed sections.

8. A reusable CF choke flange for a medical linac, the reusable CF choke flange comprising:
   a choke groove; and
   a first CF groove comprising a first knife-edge, wherein the choke groove is disposed radially inwards from the first CF groove on the reusable CF choke flange, wherein the reusable CF choke flange comprises a waveguide aperture configured to, when the reusable CF choke flange is held in abutment with a CF cover flange comprising the waveguide aperture, allow passage of at least one of RF waves or electrons through the waveguide aperture along a waveguide.

9. The reusable CF choke flange according to claim 8, comprising one or more holes disposed therethrough and configured to receive an attachment member.

10. The reusable CF choke flange according to claim 9, wherein the one or more holes are configured to receive one or more bolts for coupling with one or more nuts.

11. The reusable CF choke flange according to claim 8, wherein the reusable CF choke flange has a circular cross-section, or wherein the reusable CF choke flange has a square or rectangular cross-section.

12. The reusable CF choke flange according to claim 8, wherein a plurality of reusable CF choke flanges each according to claim 11, are configurable for combining or interleaving together with a plurality of CF cover flanges to form a plurality of jointed sections.

13. A linear accelerator (linac), the linac comprising:
   a first linac component;
   a second linac component; and
   a reusable ConFlat (CF) joint of forming a non-permanent connection between the first linac component and the second linac component, wherein the reusable CF joint comprises:
      a CF choke flange comprising:
         a choke groove; and
         a first CF groove comprising a first knife-edge, wherein the choke groove is disposed radially inwards from the first CF groove on the CF choke flange;
      a CF cover flange comprising:
         a second CF groove comprising a second knife-edge and aligned with the first CF groove; and
         a gasket disposed between and in contact with the first CF groove and the second CF groove;

wherein the CF choke flange comprises a waveguide aperture configured to, when the CF choke flange is held in abutment with a CF cover flange comprising the waveguide aperture, allow passage of at least one of RF waves or electrons through the waveguide aperture along a waveguide.

14. The linac according to claim 13, wherein at least one of the first linac component or the second linac component are selected from at least one of a target section, an electron gun, a particle source, an RF window, the waveguide, a cavity of the waveguide, or a section of a cavity of the waveguide.

15. A method for forming a reusable ConFlat (CF) joint for a medical linac, the method comprising:
providing a CF choke flange, the CF choke flange comprising:
a choke groove; and
a first CF groove comprising a first knife-edge, wherein the choke groove is disposed radially inwards from the first CF groove on the CF choke flange;
providing a CF cover flange, the CF cover flange comprising:
a second CF groove comprising a second knife-edge and aligned with the first CF groove;
disposing a gasket between and in contact with the first CF groove and the second CF groove; and
holding the CF choke flange and the CF cover flange in abutment using an attachment member, wherein the CF choke flange comprises a waveguide aperture configured to, when the CF choke flange is held in abutment with a CF cover flange comprising the waveguide aperture, allow passage of at least one of RF waves or electrons through the waveguide aperture along a waveguide.

16. The method of claim 15, wherein holding the CF choke flange and the CF cover flange in abutment using the attachment member comprises:
disposing one or more bolts though one or more respective holes in the CF choke flange and the CF cover flange; and
coupling a respective one of one or more nuts to a respective one of the one or more bolts, wherein the CF choke flange and the CF cover flange are separably coupled to enable separation thereof by uncoupling the one or more nuts from the one or more bolts.

17. The method of claim 15, wherein holding the CF choke flange and the CF cover flange in abutment using the attachment member comprises:
clamping the CF choke flange to the CF cover flange, wherein the CF choke flange and the CF cover flange are separably coupled to enable separation thereof by removing one or more clamps from the CF choke flange and the CF cover flange.

18. The method of claim 15, wherein the CF choke flange and the CF cover flange are not brazed or welded together.

19. The method of claim 15, further comprising:
disassociating the CF choke flange from the CF cover flange via the reusable CF joint by removing the attachment member;
servicing a component coupled to at least one of the CF choke flange or to the CF cover flange; and
re-coupling the CF choke flange with the CF cover flange via the reusable CF joint by reapplying the attachment member.

20. The method of claim 15, further comprising:
disassociating the CF choke flange from the CF cover flange via the reusable CF joint by removing the attachment member, and
coupling the CF choke flange to a second CF cover flange using the attachment member or coupling the CF cover flange to a second CF choke flange using the attachment member.

* * * * *